US006231532B1

(12) United States Patent

Watson et al.

(10) Patent No.: US 6,231,532 B1

(45) Date of Patent: May 15, 2001

(54) METHOD TO AUGMENT BLOOD CIRCULATION IN A LIMB

(75) Inventors: Kristin L. Watson, North Attleboro; Joseph R. Plante, Medway; Ryan A. Amara, Lynn, all of MA (US)

(73) Assignee: Tyco International (US) Inc., Exeter, NH (US)

( * ) Notice: Subject to any disclaimer, the term of this patent is extended or adjusted under 35 U.S.C. 154(b) by 0 days.

(21) Appl. No.: 09/166,480

(22) Filed: Oct. 5, 1998

(51) Int. Cl.[7] .......... A61M 9/00

(52) U.S. Cl. .......... 601/150; 601/148

(58) Field of Search .......... 601/6, 11, 148, 601/149, 150, 151, 152; 128/898; 602/13

(56) References Cited

U.S. PATENT DOCUMENTS

| | | | |
|---|---|---|---|
| 2,674,231 | 4/1954 | Erickson . | |
| 2,699,165 | 1/1955 | Ferrier . | |
| 2,781,041 | 2/1957 | Weinberg . | |
| 3,826,249 | 7/1974 | Lee et al. . | |
| 3,896,794 | 7/1975 | McGrath . | |
| 4,044,759 * | 8/1977 | Ghayouran | 601/152 |
| 4,066,084 | 1/1978 | Tillander . | |
| 4,086,920 | 5/1978 | Miniere . | |
| 4,186,732 * | 2/1980 | Christoffel | 601/150 |
| 4,204,547 | 5/1980 | Allocca . | |
| 4,311,135 | 1/1982 | Brueckner et al. . | |
| 4,396,010 | 8/1983 | Arkans . | |
| 4,583,522 | 4/1986 | Aronne . | |
| 4,738,249 | 4/1988 | Linman et al. . | |
| 4,781,189 * | 11/1988 | Vijil-Rosales | 601/152 |
| 5,022,387 | 6/1991 | Hasty . | |
| 5,050,613 | 9/1991 | Newman et al. . | |
| 5,109,832 | 5/1992 | Proctor et al. . | |
| 5,117,812 | 6/1992 | McWhorter . | |
| 5,186,163 * | 2/1993 | Dye | 601/151 |
| 5,218,954 * | 6/1993 | Van Bemmelen | 602/13 |
| 5,372,573 | 12/1994 | Habib . | |
| 5,437,610 | 8/1995 | Cariapa et al. . | |
| 5,458,562 * | 10/1995 | Cooper | 601/151 |
| 5,566,677 | 10/1996 | Raines et al. . | |
| 5,575,762 * | 11/1996 | Peeler et al. | 601/152 |
| 5,588,954 | 12/1996 | Ribando et al. . | |
| 5,588,955 | 12/1996 | Johnson, Jr. et al. . | |
| 5,626,556 * | 5/1997 | Tobler et al. | 601/151 |
| 5,630,424 | 5/1997 | Raines et al. . | |
| 5,634,889 * | 6/1997 | Gardner et al. | 601/151 |
| 5,669,872 * | 9/1997 | Fox | 601/152 |
| 5,674,262 * | 10/1997 | Tumey | 607/48 |
| 5,711,760 | 1/1998 | Ibrahim et al. | 601/149 |

(List continued on next page.)

FOREIGN PATENT DOCUMENTS

| | | |
|---|---|---|
| 0 698 387 A1 | 2/1996 | (EP) . |
| WO 95/01770 | 1/1995 | (WO) . |
| WO 96/28088 | 9/1996 | (WO) . |

* cited by examiner

*Primary Examiner*—Justine R. Yu

(74) *Attorney, Agent, or Firm*—Weingarten, Schurgin, Gagnebin & Hayes LLP

(57) ABSTRACT

A method for augmenting blood circulation in the limb of a patient is provided by customizing the compression cycle based upon patient venous characteristics. The method measures the venous refill time of the patient for use with an intermittent pneumatic compression device. A limb such as a leg is wrapped with a compression sleeve having at least one pressurizable chamber. The chamber is pressurized for a predetermined period of time to compress the limb and cause blood to flow out of the limb. The chamber is depressurized until the pressure in the chamber reaches a lower value, and the chamber is closed. The pressure in the chamber is sensed and the venous refill time, the time for the limb to refill with blood, is determined by sensing when the pressure reaches or will reach a plateau. The venous refill time is used as the basis for the time between subsequent compression pulses of the compression device.

24 Claims, 4 Drawing Sheets

U.S. PATENT DOCUMENTS

| | | | | |
|---|---|---|---|---|
| 5,715,828 | | 2/1998 | Raines et al. . | |
| 5,718,232 | | 2/1998 | Raines et al. . | |
| 5,724,981 | | 3/1998 | Apple . | |
| 5,725,485 | | 3/1998 | Ribando et al. | 601/152 |
| 5,730,136 | | 3/1998 | Laufer et al. . | |
| 5,741,294 | | 4/1998 | Stromberg | 606/201 |
| 5,749,853 | | 5/1998 | O'Donnell et al. | 604/97 |
| 5,830,164 | * | 11/1998 | Cone et al. | 601/152 |
| 5,840,049 | | 11/1998 | Tumey et al. | 601/149 |
| 5,843,007 | * | 12/1998 | McEwen et al. | 601/152 |
| 5,876,359 | * | 3/1999 | Bock et al. | 601/150 |
| 5,902,229 | | 5/1999 | Tsitlik et al. | 600/46 |
| 5,904,145 | | 5/1999 | Reid . | |
| 5,904,666 | | 5/1999 | DeDecker et al. | 604/65 |
| 5,931,797 | * | 8/1999 | Tumey et al. | 601/152 |

METHOD TO AUGMENT BLOOD CIRCULATION IN A LIMB

CROSS REFERENCE TO RELATED APPLICATIONS

N/A

STATEMENT REGARDING FEDERALLY SPONSORED RESEARCH OR DEVELOPMENT

N/A

BACKGROUND OF THE INVENTION

The velocity of blood flow in a patient's legs is known to decrease during confinement in bed. Such pooling or stasis of blood is particularly pronounced during surgery, immediately after surgery, and when the patient has been confined to bed for an extended period of time. Additionally, blood stasis is a significant cause leading to the formation of thrombi in the patient's legs, which may eventually cause serious injury or even death. Additionally, in certain patients, it is desirable to move fluid out of interstitial spaces in extremity tissues in order to reduce swelling associated with edema in the extremities. By enhancing the circulation in the limb, the arterial and venous blood flow could be improved.

Intermittent pneumatic compression (IPC) devices are used to improve circulation and minimize the formation of thrombi in the limbs of patients. These devices typically include a compression sleeve or garment which wraps around the patient's limb. The sleeve has one or more separate inflatable chambers which are connected to a source of compressed fluid, generally air. The chamber or chambers are inflated to provide a compressive pulse to the limb, thereby increasing blood circulation and minimizing the formation of thrombi. In a multi-chambered sleeve, the compression pulses typically begin around the portion of the limb farthest from the heart, for example, the ankle, and progress sequentially toward the heart. The chamber or chambers are maintained in the inflated state for a predetermined duration, and all the chambers are depressurized simultaneously. After another predetermined period of time, the compression pulse repeats. Typical compression devices are described in U.S. Pat. No. 4,396,010 and U.S Pat. No. 5,876,359, filed Nov. 14, 1994, the disclosures of which are incorporated herein by reference.

Deep vein thrombosis and other venous and arterial conditions may also be diagnosed and evaluated by various air plethysmography techniques. These techniques use one or more pressure cuffs wrapped around one or more portions of a patient's limb. Volume changes of blood flow in the limb are monitored by monitoring the pressure in the cuff or cuffs with the limb in various positions and due to various position changes of the limb, often after application of a venous tourniquet to cause the limb to fill with blood. The venous tourniquet may be applied by a pressure cuff around a portion of the limb, for example, the thigh.

SUMMARY OF THE INVENTION

The present invention relates to a method for augmenting blood flow by applying pressure to a limb and determining the time for the venous system in a limb to refill with blood. The venous refill time is then used as the depressurization time between compression pulses for subsequent compression cycles of an intermittent pneumatic compression device.

More particularly, pulses of compressed gas to a compression sleeve wrapped around a limb cause blood to flow toward the patient's body or heart. When the sleeve is depressurized, causing the chamber or chambers to deflate, the venous system in the limb refills with blood and eventually returns to a steady state. The time in which the venous system refills and returns to a steady state varies from patient to patient. Accordingly, the present invention provides a method of sensing the venous refill time. This time is used to adjust the depressurization time between pulses. By adjusting the depressurization time in this manner, compressive pulses can be provided to the limb once it has refilled, rather than waiting a predetermined or standard time, such as 60 seconds, which may be longer than desired. This allows blood flow to be customized and augmented over time for each individual patient and minimizes the time that blood is allowed to pool in the limb.

The venous refill time is preferably determined by monitoring the pressure in the chamber of the sleeve while the limb refills with blood and sensing when the pressure reaches a plateau, which indicates that the limb has refilled with blood and reached a steady state. In a multi-chambered sleeve, the pressure may be monitored in one of the chambers, for example, the middle or calf chamber of a sleeve for the leg. Alternatively, the venous refill time can be sensed by applying a venous tourniquet to the patient's limb and measuring the time for the limb to engorge with blood, since no venous flow would be allowed past the tourniquet. The tourniquet can be applied by inflating a thigh chamber of a multi-chambered sleeve.

The venous refill time can be determined at start up to set the depressurization time. Additionally, the venous refill time can be determined periodically during use of the sleeve on the patient and the depressurization time adjusted accordingly as necessary.

BRIEF DESCRIPTION OF THE DRAWINGS

The invention will be more fully understood from the following detailed description taken in conjunction with the accompanying drawings in which.

DETAILED DESCRIPTION OF THE INVENTION

Figure 1:
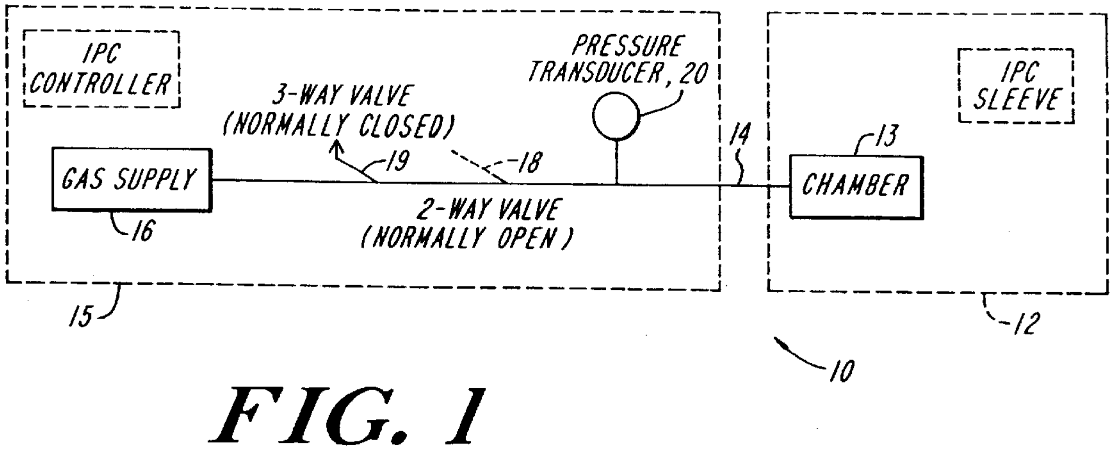
FIG. 1 is a pneumatic circuit implemented with a single-chambered sleeve for use with the method of the present invention.

FIG. 1 illustrates a pneumatic circuit with an intermittent pneumatic compression (IPC) device 10 to determine venous refill time according to the present invention. In the IPC device, a compression sleeve 12 having a single chamber 13 is connected, for example, via tubing 14, to a controller 15 having an gas supply 16 which provides compressed gas to the chamber of the sleeve. A two-way normally open valve 18 and a three-way normally closed valve 19 are provided between the sleeve 12 and the gas supply 16. A pressure transducer 20 downstream of the valve 18 monitors the pressure in the chamber.

Figure 3:
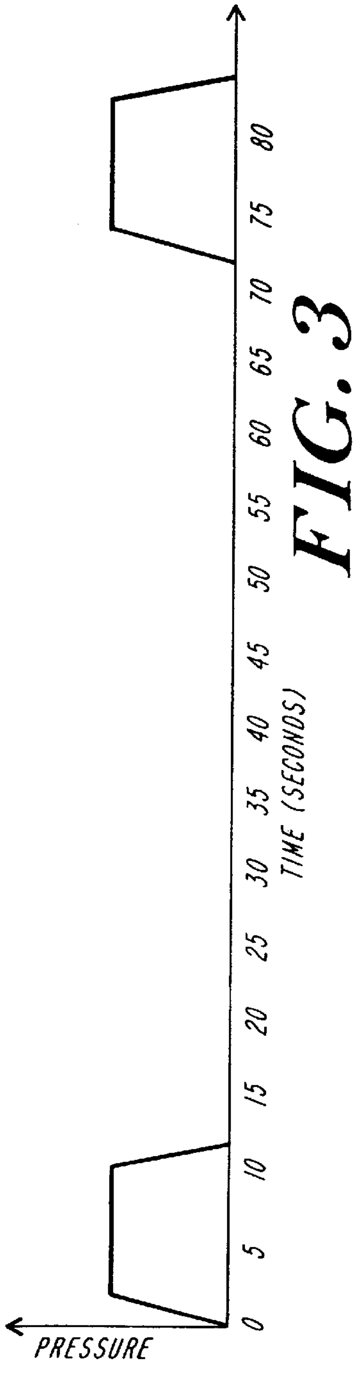
FIG. 3 PRIOR ART
FIG. 3 is a graph illustrating a prior art compression cycle.

In operation, the sleeve 12 is wrapped about a patient's leg. To provide a compressive pulse to the leg, the valve 19 is opened and the gas supply 16 is activated to provide compressed gas to the chamber 13 until the pressure in the chamber reaches a suitable value for operation in a compression cycle, as is known in the art. Upon completion of the pressurization, the gas supply 16 is deactivated and the chamber 13 allowed to depressurize by, for example, venting back through the tubing to the controller. Gas could also vent to ambient through the three-way valve 19. A typical prior art compression cycle in which the chamber is pressurized after a standard depressurization time of approximately 60 seconds is indicated in FIG. 3.

Figure 4:
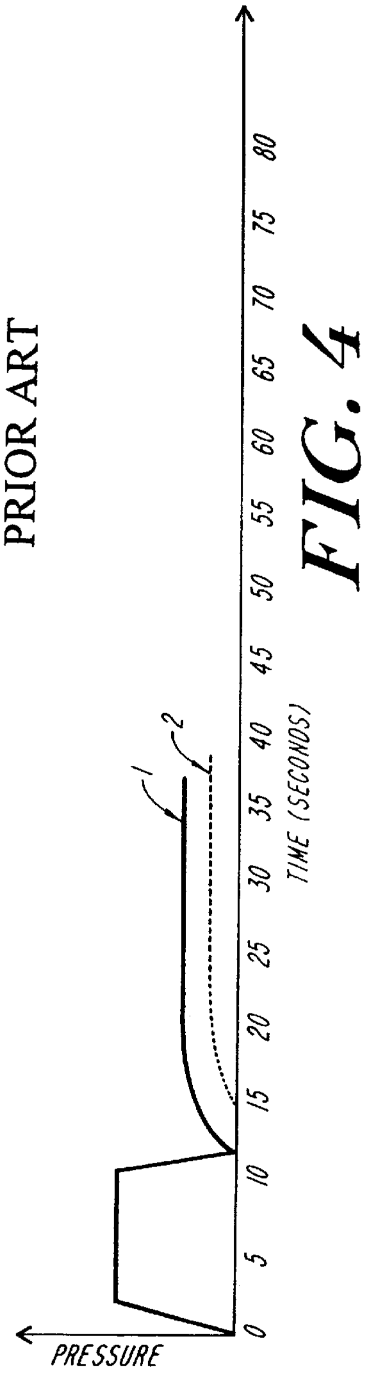
FIG. 4 is a graph illustrating a pressure profile during a procedure to determine venous refill time according to the present invention.

When it is desired to determine the venous refill time for the patient, the chamber is permitted to depressurize until the pressure in that chamber reaches a lower value, typically 10 mm Hg (after approximately 2.5 seconds of depressurization). Alternatively, the chamber could be permitted to depressurize for a predetermined period of time. The two-way valve 18 is then closed to prevent further depressurization of the chamber. Alternatively, the chamber could be allowed to depressurize fully and could then be repressurized only until the pressure reaches the predetermined value, for example, 10 mm Hg. Referring to FIG. 4, the pressure in the chamber is then sensed by the pressure transducer 20 for a time sufficient to allow the venous system in the leg to refill. The pressure rises as the leg gets larger, filling with blood. The pressure plateaus when the leg has refilled and returned to a steady state, indicated by the solid curve 1 in FIG. 4. This plateau has been shown to correlate with actual venous flow sensed by a Doppler probe and indicated by curve 2 in FIG. 4.

Figure 5:
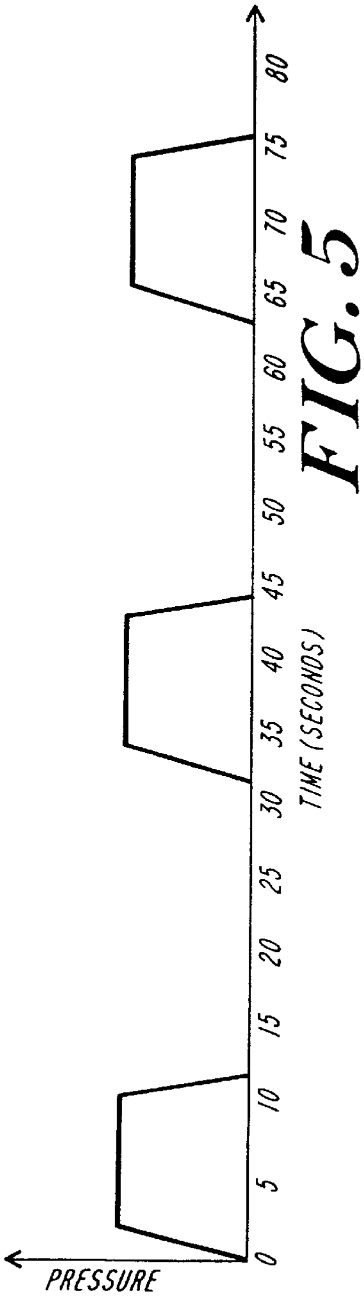
FIG. 5 is a graph illustrating a compression cycle after determining venous refill time according to the present invention.

The controller 15 may determine this plateau in various ways. For example, the controller may determine at what point the pressure rises less than a predetermined amount, such as 0.2 mm Hg, for a predetermined time, such as 10 seconds. The time between the start of depressurizing the pressurizable chamber and when this plateau occurs is determined to be the venous refill time and is taken by the controller as the basis for the depressurization time for subsequent cycles. Other formulas can be used if desired to determine the plateau. The controller can determine when the pressure actually reaches a plateau or when the pressure will reach a plateau. A compression cycle having a depressurization time of approximately 20 seconds is illustrated in FIG. 5.

The procedure for determining the venous refill time is done at least once upon start up. Preferably the time is determined after enough cycles have occurred to allow the system to settle on a desired pressure in the chamber, such as 45 mm Hg. The procedure can be performed at other times during use of the compression sleeve to update the refill time. The procedure should be done after a cycle in which the chamber has been compressed to the same desired pressure as on start up, such as 45 mm Hg.

The present method was tested on thirteen subjects. The depressurization times based upon the venous refill times were distributed as follows:

| Depressurization Time (sec) | Number of Subjects |
|---|---|
| ≦20 | 7 |
| 21–30 | 4 |
| 31–40 | 2 |

In the operation of a typical prior art IPC device, the time between compression pulses is the same for all patients, such as approximately 60 seconds. As noted above, the cycle for such a prior art device is illustrated in FIG. 3. With the present invention, the time between compression pulses may be much less than 60 seconds. A cycle in which the time between pulses is approximately 20 seconds is illustrated in FIG. 5. It is apparent from FIG. 5 that more blood can be moved over time, allowing less blood to pool, and thereby augmenting more blood flow. Blood stasis is decreased and the formation of thrombi is minimized.

The present method is also beneficial in augmenting arterial blood flow. By increasing venous blood flow, the venous pressure is reduced, thereby enhancing blood flow through the capillary vessels. In this manner, arterial blood flow is also augmented.

Figure 2:
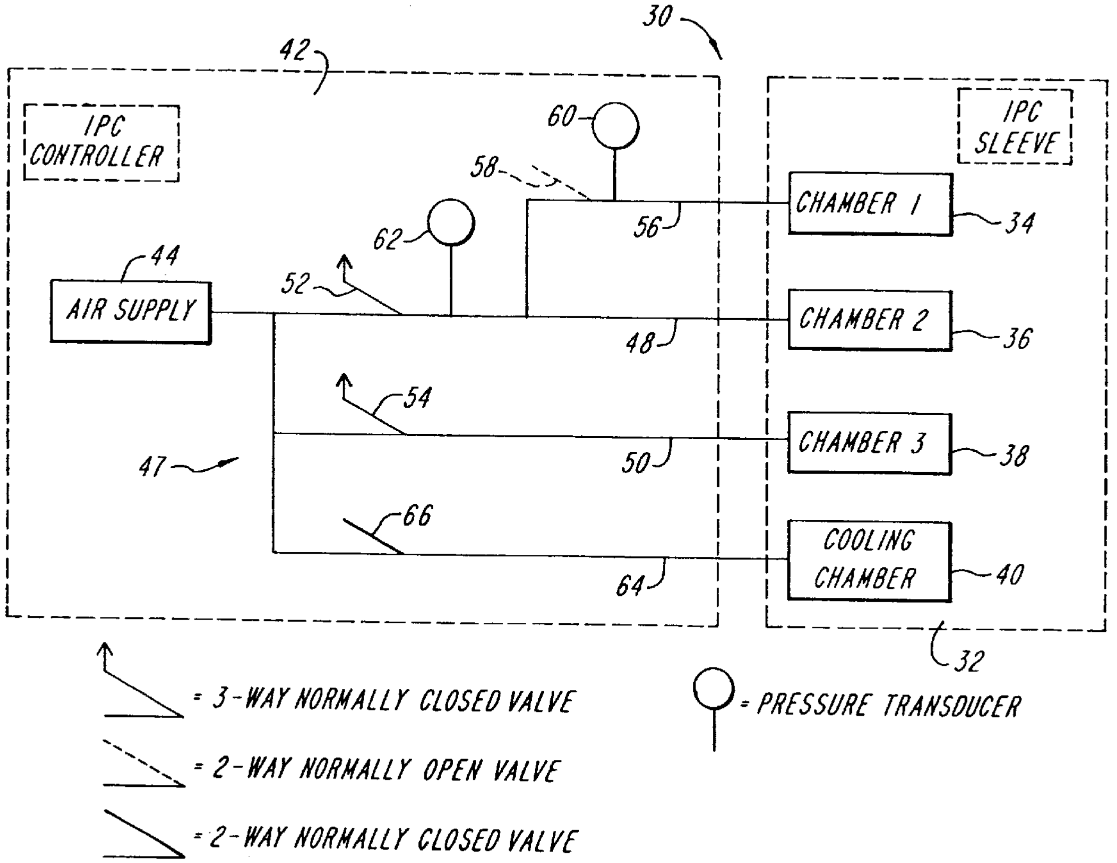
FIG. 2 is a pneumatic circuit implemented with a three-chambered sleeve for use with the method of the present invention.

An embodiment of a multi-chambered IPC device 30 operative with the present method is illustrated in the pneumatic circuit of FIG. 2. In this device, a sleeve 32 has three pressurizable chambers 34, 36, and 38, and an optional cooling chamber 40. A controller 42 has a gas supply 44 and valving 47 to distribute the gas to the chambers. In lines 48 and 50 leading to two of the chambers (chambers 2 and 3 in FIG. 2), the valving includes three-way normally closed valves 52 and 54 which include vent openings. In a line 56 leading to chamber 1, downstream from the normally closed valve of chamber 2, the valving includes a two-way normally open valve 58. A pressure transducer 60 in line 56 monitors the pressure in chamber 1, and a pressure transducer 62 in line 48 monitors the pressure in chamber 2. In a line 64 leading to the cooling chamber, the valving includes a two-way normally closed valve 66.

In operation, to provide a sequence of pulses to the limb, the two-way valve 58 is closed to close off chamber 1. The gas supply 44 is activated and the three-way valve 52 to chamber 2 is opened to allow chamber 2 to fill to the desired pressure. After a predetermined time, while valve 52 is still open, valve 58 to chamber 1 is opened to allow chamber 1 to fill. The three-way valve 54 to chamber 3 is also opened, for example, after chambers 2 and 1 have begun filling, to allow chamber 3 to fill. Upon completion of the pressurization, the gas supply 44 may be deactivated and the chambers are simultaneously depressurized, by for example, venting through vents in the three-way valves 52 and 54. During the pressurization of all the chambers, the two-way valve 66 to the cooling chamber is closed.

When it is desired to determine the venous refill time for the patient, the two-way valve 58 is closed to prevent depressurization of chamber 1 below a predetermined value, for example, 10 mm Hg. The pressure in chamber 1 is then sensed by the pressure transducer 60 for a time sufficient to allow the venous system in the leg to refill. The pressure rises as the leg gets larger, filling with blood. The pressure plateaus when the leg refills. Curve 1 of FIG. 4 as discussed above illustrates the pressure plateau when the leg refills.

Figure 6:
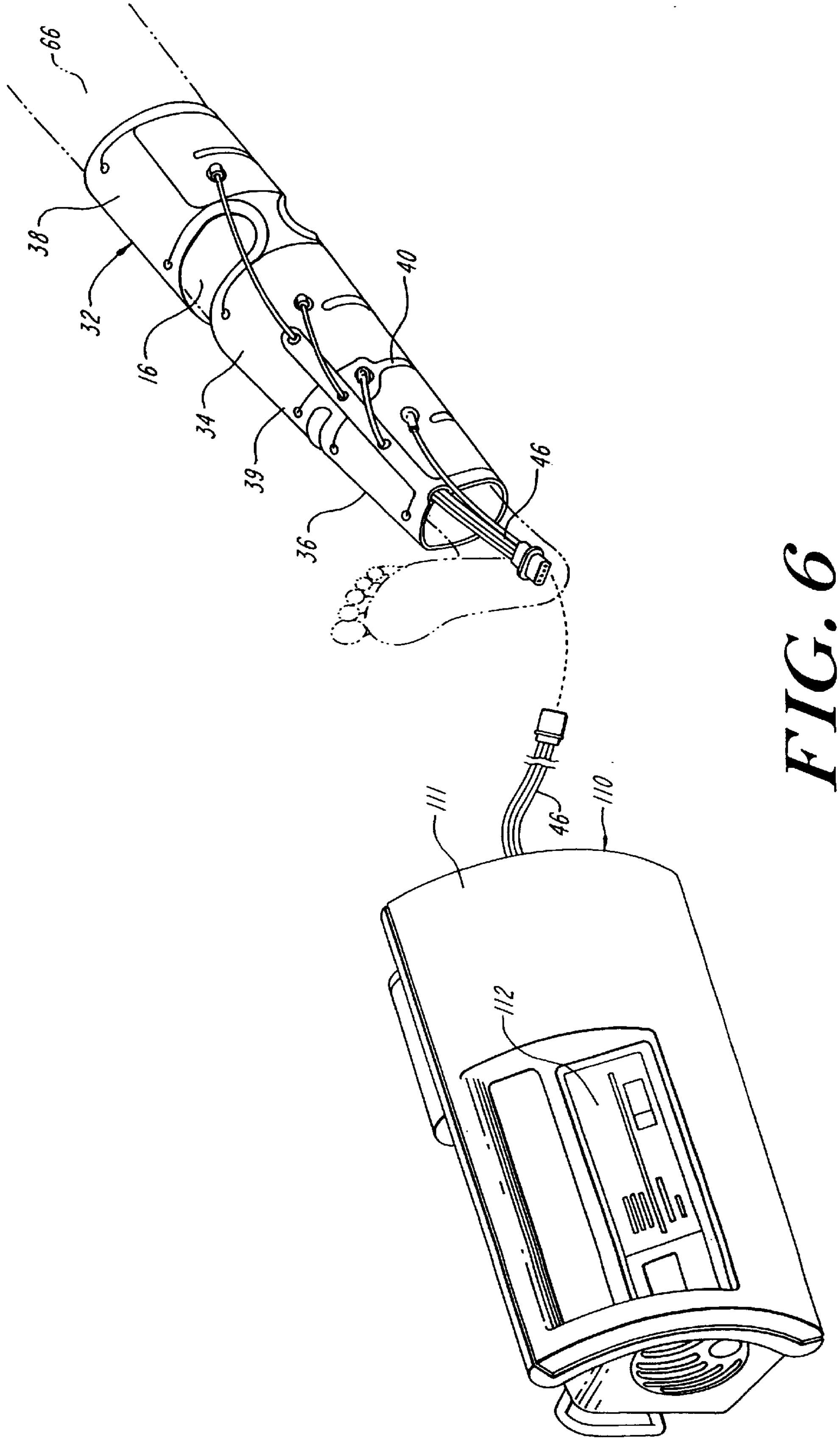
FIG. 6 is an isometric view of a compression device having a three-chambered sleeve for use with the present invention.
Figure 7:
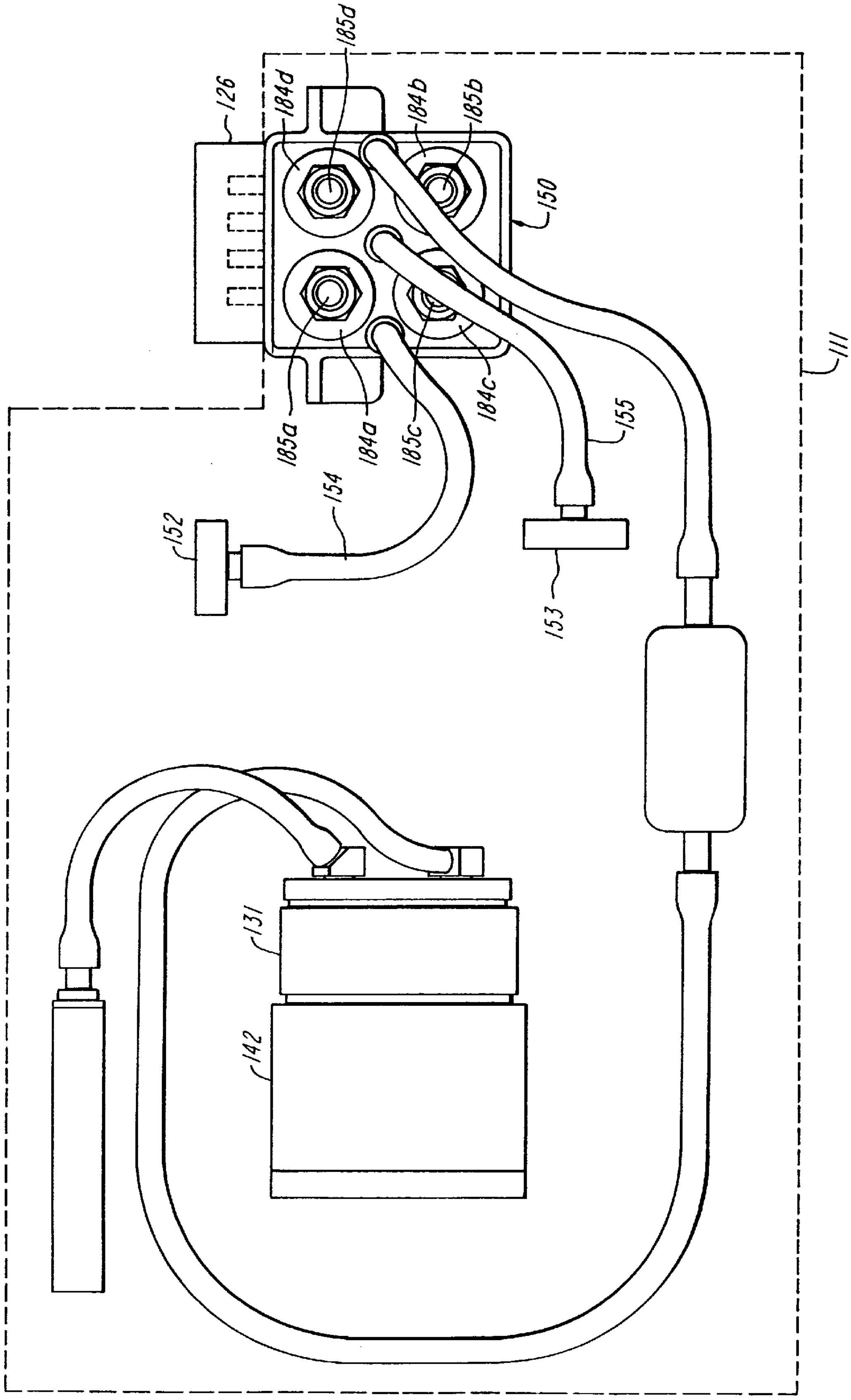
FIG. 7 is a plan view of the pneumatic apparatus of the compression device of FIG. 6.

The pneumatic circuit of FIG. 2 may be implemented as shown in FIGS. 6 and 7. In this embodiment, the compression sleeve 32 has a plurality of fluid pressure chambers 36, 34, 38 arranged around the ankle region, the calf region, and the thigh region of a leg 66 respectively. An optional cooling or ventilation channel 40 extends around the chambers and is provided with apertures or small openings on the inner surface of the sleeve to cool the leg. If employed, cooling is deactivated when the sleeve is pressurized. When the venous refill time is being determined, cooling may in some embodiments be deactivated. A conduit set 46 of four conduits leads from the controller 110 having a source of compressed gas or other fluid to the three chambers and the cooling channel for intermittently inflating and deflating the chambers and to cool the leg. In the described embodiment, the ankle chamber 36 corresponds to chamber 2 of FIG. 2, the calf chamber 34 to chamber 1 of FIG. 2, and the thigh chamber 38 to chamber 3 of FIG. 2, respectively, although it will be appreciated that this correspondence could differ. Thus, the venous refill time could be determined by monitoring the pressure in the ankle or thigh chamber or a combination of chambers.

The controller 110 is located in a housing 111. A control or front panel 112 on the front of the housing includes controls and indicators for system operation. An output connector 126 is disposed on the rear of the housing and is adapted to receive the conduit set 46 by which the controller is connected to the compression sleeve. In the interior of the housing 111, a compressor 131 is directly connected to and controlled by a motor 142. A valving manifold assembly 150 is provided to distribute compressed gas to the appropriate chambers via the conduit set.

A pressure transducer 152 is coupled via tubing 154 to the manifold assembly 150 for monitoring output pressure in one of the chambers. As shown, the transducer 152 monitors pressure in the ankle chamber. An additional pressure transducer 153 is coupled via tubing 155 to the manifold assembly 150 for monitoring pressure in another one of the chambers to determine venous refill time. As shown, the transducer 153 monitors pressure in the calf chamber. Suitable valves 185*a–d* are connected to valve seats 184*a–d*.

In another embodiment of the present invention, the pressure could be measured with the use of a venous tourniquet placed about the patient's leg. The tourniquet may be provided by the thigh chamber 38 of a multi-chambered sleeve. The time for the patient's leg to engorge with blood would then be measured, since no venous flow would be permitted by the tourniquet until the chamber is deflated. Alternatively, a nurse or other skilled person could apply and remove a separate tourniquet in conjunction with the measuring of the time for engorgement. However, the venous tourniquet is less comfortable for the patient. Thus, the previously described embodiment is considered preferable.

In a further alternative using a multi-chambered sleeve, pressure could be measured in two or more chambers during depressurization and the time to reach a plateau determined for each chamber. The venous refill time may be taken as the average of the times for each chamber.

Additionally, IPC devices typically use two sleeves, one for each leg. In this case, the pressure could be sensed in both sleeves. If the venous refill times are determined to be different in each sleeve, the longer of the two venous refill times is preferably used for both sleeves.

In some embodiments having two sleeves, a single tubing set from the controller to the sleeves is used. The tubing set extends from a single connection at the controller to a "T" junction at which the tubing set divides into two branches, one to each of the two sleeves. Since the tubing set in this configuration combines the gas from two chambers into a single line at the controller, the controller senses the longer of the two refill times if the patient has different venous characteristics in either leg.

The present method for augmenting blood flow can be implemented with other embodiments of IPC devices. For example, a pressure transducer for measuring the pressure could be located directly at one of the sleeve chambers, rather than at the controller. It will be appreciated that many embodiments of IPC devices are known in the prior art and are available commercially, and the method of the present invention is operable with such other embodiments as well. The invention is not to be limited by what has been particularly shown and described, except as indicated by the appended claims.

We claim:

1. A method for augmenting blood flow by applying pressure to a limb comprising;

(a) wrapping a limb with a sleeve having at least one pressurizable chamber;

(b) determining by sensing pressure in the at least one pressurizable chamber a time for venous blood flow in the limb to return to a steady state after a compression of the limb, the time comprising a venous refill time;

(c) performing a compression cycle comprising:

pressurizing the pressurizable chamber with a gas for a period of time sufficient to compress the limb to cause blood in the limb to flow out of the limb, and depressurizing the pressurizable chamber; and (d) repeating step (c) after a period of time based upon the venous refill time.

2. The method of claim 1, wherein in step (b), the venous refill time is determined by:

pressurizing the pressurizable chamber with a gas for a period of time sufficient to compress the limb to cause blood in the limb to flow out of the limb;

depressurizing the pressurizable chamber until the pressure in the chamber reaches a predetermined lower value or for a predetermined time;

closing the pressurizable chamber;

sensing pressure in the chamber, the pressure being an indication of blood volume change in the limb;

determining a time when the pressure reaches a plateau; and determining a venous refill time comprising the time difference between beginning the step of depressurizing the pressurizable chamber and the time when the pressure reaches the plateau.

3. The method of claim 2, wherein the step of determining the time when the pressure reaches a plateau comprises sensing a time when the pressure rises less than a predetermined amount for a second predetermined time.

4. The method of claim 3, wherein the predetermined amount comprises 0.2 mm Hg and the predetermined time comprises ten seconds.

5. The method of claim 2, wherein in step (a) the sleeve has a plurality of pressurizable chambers.

6. The method of claim 2, wherein in step (a) the sleeve has at least three pressurizable chambers.

7. The method of claim 6, wherein the pressure is sensed in a middle one of the at least three pressurizable chambers.

8. The method of claim 7, wherein the middle one of the at least three pressurizable chambers surrounds a calf region of the limb.

9. The method of claim 1, wherein in step (b) the venous refill time is determined by:

applying a venous tourniquet to the limb; and the venous refill time comprises a time for the limb to become engorged with blood.

10. The method of claim 1, wherein:

in step (a) the sleeve has a plurality of pressurizable chambers, including a chamber surrounding the thigh region and a chamber surrounding a region below the knee;

in step (b), pressurizing the chamber surrounding the thigh region to apply a venous tourniquet to the limb; and the venous refill time comprises a time for the limb to become engorged with blood.

11. The method of claim 1, further comprising repeating step (b) after one or more subsequent compression cycles to redetermine the venous refill time, and repeating step (c) after a period of time based on the redetermined venous refill time.

12. A method for measuring venous refill time in a limb to which intermittent pneumatic compression is applied, comprising:

(a) providing an intermittent pneumatic compression system for applying pressure to the limb, the system having a compression sleeve having a plurality of pressurizable chambers, a source of compressed gas in communication with the pressurizable chambers via tubing, and a controller in communication with the source of compressed gas and the tubing to control application of compressed gas to the pressurizable chambers and operative to direct compressed gas to the pressurizable chambers and depressurize the pressurizable chambers;

(b) wrapping the limb with the compression sleeve;

(c) pressurizing the pressurizable chambers with a gas for a predetermined period of time sufficient to compress the limb to cause blood in the limb to flow out of the limb;

(d) depressurizing the pressurizable chambers until pressure in one or more of the pressurizable chambers reaches a lower value;

(e) closing at least the one of the pressurizable chambers;

(f) sensing pressure in at least the one of the pressurizable chambers, the change in pressure being an indication of blood volume change in the limb;

(g) determining a venous refill time comprising the time difference from the beginning of the step of depressurizing the pressurizable chambers until a time when the pressure reaches a plateau; and (h) depressurizing subsequent compression cycles for a period of time based on the venous refill time.

13. The method of claim 12, further comprising repeating steps (b) through (g) periodically after one or more of the subsequent compression cycles to redetermine the venous refill time; and depressurizing further subsequent compression cycles for a period of time based on the redetermined venous refill time.

14. The method of claim 12, wherein in step (f), the pressure is sensed by a pressure transducer provided at the controller.

15. The method of claim 12, wherein in step (f), the pressure is sensed by a pressure transducer provided at the compression sleeve.

16. A method for augmenting blood flow by applying pressure to a limb, comprising:

wrapping the limb with a sleeve having at least one pressurizable chamber;

pressurizing the pressurizable chamber with a gas for a period of time sufficient to compress the limb to cause blood in the limb to flow out of the limb;

depressurizing the pressurizable chamber until the pressure in the chamber reaches a lower value;

closing the pressurizable chamber;

sensing pressure in the chamber, the pressure being an indication of blood volume change in the limb;

determining a time when the pressure reaches a plateau;

determining a venous refill time comprising the time difference between beginning the step of depressurizing the pressurizable chamber and the time when the pressure reaches the plateau; and depressurizing subsequent compression cycles for a period of time based on the venous refill time.

17. The method of claim 16, wherein the step of determining when the pressure reaches a plateau comprises sensing when the pressure rises less than a predetermined amount for a predetermined time.

18. The method of claim 16, wherein the predetermined amount comprises 0.2 mm Hg and the predetermined time comprises ten seconds.

19. A method for augmenting blood flow by applying pressure to two limbs of a patient, comprising:

wrapping a first limb with a first sleeve having a first pressurizable chamber and wrapping a second limb with a second sleeve having a second pressurizable chamber;

pressurizing the first and second pressurizable chambers with a gas for a predetermined period of time sufficient to compress the first and second limbs to cause blood in the first and second limbs to flow out of the first and second limbs;

depressurizing the first and second pressurizable chambers until the pressure in both of the first and second pressurizable chambers reaches a lower value;

closing the first and second pressurizable chambers;

sensing the pressure in the first and second pressurizable chambers, a change in pressure being an indication of blood volume change in the first and second limbs;

determining a time from beginning the depressurizing of the first and second pressurizable chambers until the pressure reaches a plateau in both of the first and second pressurizable chambers, the time comprising a venous refill time; and depressurizing subsequent compression cycles in the first and second sleeves for a period of time based on the venous refill time.

20. The method of claim 12, wherein in the step of sensing the pressure, the pressure is a combined pressure in the first and second pressurizable chambers.

21. The method of claim 2, wherein the step of determining when the pressure reaches a plateau comprises determining when the pressure actually reaches a plateau.

22. The method of claim 2, wherein the step of determining a time when the pressure reaches a plateau comprises determining when the pressure will reach a plateau.

23. The method of claim 16, wherein the step of determining a time when the pressure reaches a plateau comprises determining when the pressure actually reaches a plateau.

24. The method of claim 16, wherein the step of determining a time when the pressure reaches a plateau comprises determining when the pressure will reach a plateau.

* * * * *